United States Patent [19]
Herskovits

[11] 3,992,780
[45] Nov. 23, 1976

[54] MOUTH IMPLANT, A METHOD OF INSERTING THE IMPLANT IN THE MOUTH, AND A TOOL FOR MACHINING THE DENTAL ARCH OF THE JAW FOR RECEPTION OF THE IMPLANT

[76] Inventor: Imre Herskovits, Via Gaggini da Bissone 6, 6900 Lugano, Switzerland

[22] Filed: Feb. 21, 1975

[21] Appl. No.: 551,587

[30] Foreign Application Priority Data
May 9, 1974 Switzerland.......................... 6469/74

[52] U.S. Cl. ............................... 32/10 A; 128/92 C
[51] Int. Cl.² .......................................... A61C 13/00
[58] Field of Search ................... 32/10 A, 40 R, 59; 128/92 C

[56] References Cited
UNITED STATES PATENTS

| | | | |
|---|---|---|---|
| 2,133,859 | 10/1938 | Hawley | 128/92 D |
| 2,757,455 | 8/1956 | Birnbaum | 32/59 |
| 3,579,829 | 5/1971 | Sampson | 32/10 A |
| 3,660,899 | 5/1972 | Linkow | 32/10 A |
| 3,708,883 | 1/1973 | Flander | 32/10 A |
| 3,729,825 | 5/1973 | Linkow et al. | 32/10 A |
| 3,928,914 | 12/1975 | Kozlovsky | 32/10 A |

*Primary Examiner*—Louis G. Mancene
*Assistant Examiner*—Jack Q. Lever
*Attorney, Agent, or Firm*—Young & Thompson

[57] ABSTRACT

An implant is placed in the jaw of a patient by cutting spaced slots in the patients jaw and locating the side plates of a U-shaped implant in the slots. The side plates are arranged so that the healing of the jaw, by fibrogenetic and osteogenetic neoformation, results in the implant becoming anchored in the jaw, and the implant is adapted for the reception of a stump, preferably a screw threaded stump to serve as an artificial tooth on a mounting for such a tooth.

11 Claims, 10 Drawing Figures

MOUTH IMPLANT, A METHOD OF INSERTING THE IMPLANT IN THE MOUTH, AND A TOOL FOR MACHINING THE DENTAL ARCH OF THE JAW FOR RECEPTION OF THE IMPLANT

FIELD OF THE INVENTION

This invention relates to an implant, known in dental surgery as an endoosseous implant for ondontostomatology, a method for insertion of the implant in the jaw bone, and a tool for cutting the jaw bone for reception of the implant.

BACKGROUND OF THE INVENTION

In U.S. Pat. Ser. No. 3,577,853, German Offenlegungsachrift No. 1,939,055 and French Patent No. 2,133,656 there are disclosed endoosseous implants comprising a single plate. To install such implants, it is required to make a wide fissure or slot in the jaw bone, which slot requires to be in the region of 3–4 mm. in width. The healing of such a fissure takes a substantial period of time (more than 15 days) and this delay can give rise to complications.

Indeed, the considerable difficulties in implanting individual endoosseous implants for ondontostomatology (mouth surgery) for the partial or full substitution of teeth are well known. The difficulties arise because known individual implants fail to satisfy the many requirements of present technology in this field.

OBJECTIVES OF THE PRESENT INVENTION

The present invention has as a main objective to provide an individual endoosseous implant for ondontostomatology (mouth surgery), a method for inserting the implant in the jaw bone and a tool for use in carrying out the method, whereby the disadvantages of the known implants, tools and methods, are avoided.

Another objective of the invention is to provide an implant which will anchor more securely in the jaw, and by the use of which the time for healing of the jaw after insertion of the implant, is much reduced.

Another objective of the invention is to provide a method of inserting an implant whereby only two narrow slots are made in the jaw, for the greater comfort of the patient, as well as ensuring that healing time is kept to a minimum.

Yet another objective of the invention is to provide a tool for the cutting of the jaw for the reception of the implant, which will permit of a rapid, simple operation on of the jaw without requiring the any additional cutting of the jaw.

BRIEF DESCRIPTION OF THE INVENTION

Figures 1, 2:
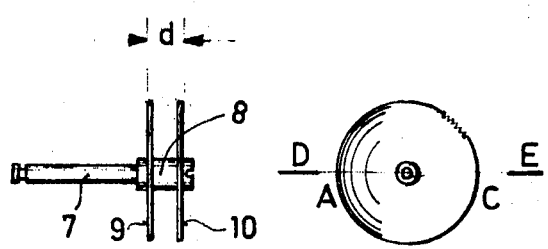
FIG. 1 shows in side view a tool adapted for cutting slots in the jaw bone and for the reception of the implant illustrated in FIGS. 3, 4 and 5.
FIG. 2 shows a front view of a tool shown in FIG. 1.

According to the invention an endoosseous implant comprises means defining a base from which extend two upstanding, spaced side plates, said plates being profile shaped or as to be capable of being received in two slots formed in a dental arch portion of the jaw bone by means of rotary disc cutters, and being such as to become anchored in the dental arch portion of the jaw bone upon healing by fibrogenetic and osteogenetic neoformation of the said dental arch portion, said base being adapted to receive one or more stumps which can serve as artificial teeth or mountings for artificial teeth.

Preferably, the means defining the base comprises two cross plates each of which is adapted to receive a stump. In a preferred case, the means defining the base, for the reception of the or each stump, is screw threaded, to receive screw threaded stumps. In practice, it will be useful to provide one or more stumps in combination with the implant.

It is preferred that the side plates should be of semi-circular configuration, or at least the profile should be derived from a semi-circle. The plates are preferably identical and lie in parallel, spaced planes.

For the anchoring of the plates in the dental arch of the jaw bone, the plates preferably have holes through which new growth of a fibrogenetic and osteo genetic nature takes place, in effect embedding the implant in the bone.

The means defining the base may be such that when the stump or stumps are attached thereto the stump or stumps lie at an angle to a mid-plane between the plates. This would be desirable where the stumps or mouldings to define teeth are mounted thereon and are required to fit in with the surrounding teeth or gum shape, in order that normal mastication can take place.

It is of course desirable that the implant should be of a material which is not attacked by the normal acidic food stuffs, beverages and other solutions which are inserted into or exist in the mouth, and a particularly good material is spectrographically pure tantalum.

In a preferred case the thickness of each of the side plates is 0.4 mm., and the cross spaces defining the base are preferably of 0.8 mm. width.

By forming two narrow slots in the bone, and inserting the implant, it has been found that the bone and flesh heals in as little as 5 or 6 days and this has the advantage that the possibility of complications arising is much reduced.

By reducing the thickness of the slots formed in the bone, the healing time can be reduced even further, and it is felt that the width of the slots may be reduced to as little as 0.3 m.m.

Also according to the present invention there is provided a method of inserting an implant asforesaid in a dental arch portion of a patient's jaw bone, wherein two slots of sufficient diameter to receive the side plates of the implant are cut in the dental arch portion by means of rotating cutter discs, the spacing and disposition of the slots one to the other corresponding to the spacing and disposition of the side plates of the implant one another, the implant is positioned by inserting the side plates respectively in the said slots, allowing the implant to become anchored by fibrogenetic and osteogenetic neoformation, and attaching one or more stumps to the anchored implant, including, if necessary, final adaption and alignment of the or each stump.

In the preferred case, the implant is threaded to receive the stump or stumps in screw threaded fashion, and the stump or stumps is or are appropriately screw threaded.

In a particularly advantgeous arrangement, the slots are cut by two parallel, spaced cutter discs mounted on a common shaft and spaced by a spacer boss, and in cutting the slots, the cutter discs are caused to penetrate into the dental arch portion of the bone until the spacer contacts the said dental arch portion, the height and profile of the side plates of the implant corresponding to the depth and profile of the slots.

Also in accordance with the present invention there is provided a tool for cutting the said slots by the method as set forth herein, said tool comprising a shaft carrying parallel cutter discs, spaced by a spacer boss.

Figure 4:
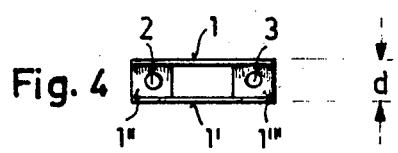
FIG. 4 shows the implant of FIG. 3 in bottom plan view.
Figure 3:
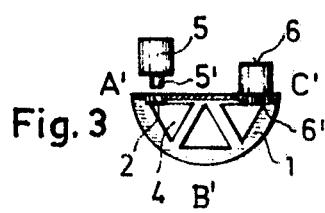
FIG. 3 shows in side view, one embodiment of an implant according to the invention and which is provided with two stumps.
Figure 5:
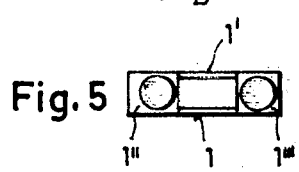
FIG. 5 shows the implant of FIG. 3 in plan view.
Figure 9:
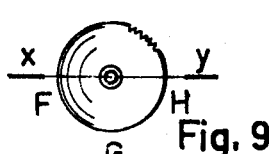
FIGS. 9 and 10 show in end view and in side view respectively the tool which serves to make the slots in the bone for the reception of the implant shown in FIGS. 7 and 8.

Referring now, to the drawing in more detail, and firstly to FIGS. 3, 4 and 5, the implant comprises two parallel plates 1 and 1' having a profile made up of a curved portion which is almost a semi-circle and a straight portion as shown. The plate has openings, or other equivalent means, for retention of the plates in the bone resulting from the growth of the bone cells and tissues cells which envelop the implant after some days following its insertion in the bone. The two plates are connected along the straight portions by one or more connecting plates 1'' and 1''' drilled and threaded to receive the stumps 5 and 6 which are threaded on reduced diameter portions 5' and 6'. Those stumps may in themselves form artificial teeth, or may form mountings for full or portions of artificial teeth.

The two plates 1 and 1' are parallel and spaced by the distance $d$. This distance is calculated depending upon the bone structure of the mouth of the particular patient in which the implant is to be inserted, and is to some extend dependent upon other characteristics of the mouth.

Figure 6:
FIG. 6 shows in side view an implant according to another embodiment of the invention and having a single stump.

For the quick and accurate insertion of the implant in the jaw bone, the bone is slotted by means of the tool shown in FIGS. 1 and 2. This tool comprises two cutter discs 9 and 10 which are mounted on the shaft 7. The discs 9 and 10 are held apart by spacer boss 8 which can if desired, be dispensed with, and in such case the discs 9 and 10 would be directly connected to the shaft 7. The cutter discs 9 and 10 have diameters which correspond exactly to that of the semi-circular profiles of the plates 1 and 1' of the implant. Thus, the arc ABC of the discs 9 and 10 corresponds exactly to the arc A'B'C' of the implant shown in FIGS. 3 and 6. In addition, the distance $d$ (FIG.1) spacing the two disc cutters 9 and 10 is exactly the same as the distance $d$ spacing the two plates 1 and 1' as shown in FIG. 4. Furthermore, the thickness of each of the two disc cutters 9 and 10 is exactly equal to that of each of the two plates 1 and 1' of the implant, so that in using the tool of FIG. 1 to form the slots, there are formed in the jaw bone of the appropriate dental arch portion in which the implant is to be inserted, two parallel, semi-circular slots of a depth corresponding exactly to the height of the plates 1 and 1' and also corresponding in thickness to the thickness of those plates.

Figure 8:
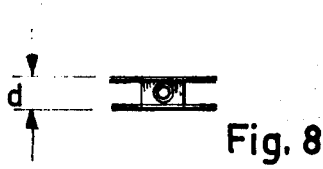
FIGS. 7 and 8 respectively illustrate in side and in bottom plan view, an implant according to another embodiment of the invention.
Figure 7:
Figure 10:
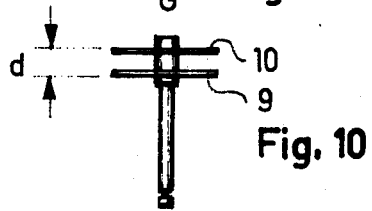

The implant is appropriately positioned in the dental arch by insertion of the plates in these slots, and is left for a few days until it becomes anchored in the dental arch as the result of fibrogenetic and osteogenetic neoformation. Next, the bores 2 and 3 are cleared of any obstructions therein, and the stumps 5 and 6 are subsequently screwed into the bores so as to compress the gums and prevent the penetration of saliva. In FIGS. 7 and 8 there is shown an embodiment of the invention in which the implant is generally smaller, the radius of curvature of the semi-circular profile of the plates being smaller and the distance $d$ being smaller than in the case of the previously described embodiment. For the insertion of such smaller version, the disc cutters 9 and 10 as shown in FIG. 10 will be smaller.

Referring again to FIG. 1, it is to be noted that the diameter of the spacer bush 8 of the shaft 7 which separates the two cutter discs 9 and 10, is such that the difference between the radius of each cutter disc 9 and 10, and that of the bush 8 is equal exactly to the depth of insertion of the implant. That is to say, the height of each plate 1 and 1'. It is furthermore to be noted that the stumps 5 and 6 may be arranged so as to lie at an angle to the median plane between the plates 1 and 1'. It is preferred that the stumps 5 and 6 should have axes which are parallel one with the other. The inclination of the stumps will be arranged to suit the general disposition of the other teeth in the patient's mouth, and to facilitate normal mastication.

In a practical embodiment of the invention, the thickness of each of the plates 1 and 1' of the implant may be 0.4 mm., and that of the upper plates 4'' and 1''' would also be 0.4 mm., except where the plate has the threaded bore or bores to receive the stump or stumps. At such region, the thickness preferably would be 0.8 m.m. in view of the fact that this region has to receive the threaded stump. The material of the implant must of course be inert to the biochemical, physical and bioelectrical corrosion erosion which can arise as a result of general conditions in the mouth. The material is preferably selected from the noble metals and in a particularly suitable arrangement, it is constructed of tantalum of high spectrographic purity.

The shape and number of the openings 4 and stumps 5 and 6 may vary as may the number of the upper plates 1'' and 1''', without departing from the scope of the invention.

Furthermore, the profile of the plates 1 and 1' may be different from the semi-circular configuration shown, although it is preferred that these profiles be derived from the semi-circular. For example, the profiles may be semi-polygonal or the like.

We claim:

1. An endoosseous implant which comprises a base, a pair of upstanding spaced parallel side plates of thin metal of substantially uniform thickness, said plates being disposed at a distance from each other equal to the distance between two spaced parallel slots cut in the middle portion of each side part of the cortical jaw bone in which said plates are to be inserted, said implant being U-shaped in a sectional plane perpendicular to the planes of said plates, and means on said base for receiving at least one stump for at least one artificial tooth.

2. An implant as claimed in claim 1, said base comprising two cross plates spaced from each other and each interconnecting said two side plates, each said cross plate having means to receive thereon a said stump.

3. An implant as claimed in claim 1, said base comprising a single cross piece.

4. An implant as claimed in claim 1, said receiving means comprising an internally screw-threaded opening through said base.

5. An implant as claimed in claim 1, in combination with at least one said stump.

6. An implant as claimed in claim 1, said side plates being of part-circular shape.

7. An implant as claimed in claim 1, said plates having holes therethrough whereby the implant becomes anchored in said jaw bone by osteogenetic growth through said holes.

8. An implant as claimed in claim 1, said plates having each a thickness of about 0.4 mm. and said base having a thickness of about 0.8 mm.

9. A method of inserting an implant in a dental arch portion of a patient's jaw bone, comprising cutting a pair of parallel slots in the middle portion of the cortical jaw bone by means of a pair of rotating cutter discs that are coaxial and parallel to each other and spaced apart a distance equal to the distance between side plates of an implant to be placed in the jaw bone, positioning a said implant by inserting side plates of the implant in said slots, allowing the implant to become anchored in the jaw by osteogenetic neoformation, and screwing a tooth stump to the anchored implant.

10. A method as claimed in claim 9, and providing between said cutter discs a hub, and predetermining the depth of cut by cutting into the jaw bone until said hub contacts the jaw bone.

11. A method as claimed in claim 9, and providing holes through said side plates through which said osteogenetic neoformation takes place.

* * * * *